(12) United States Patent
Belz et al.

(10) Patent No.: US 9,588,133 B2
(45) Date of Patent: Mar. 7, 2017

(54) ANALYTICAL SYSTEM WITH TIP RACK ASSEMBLY CONFIGURED TO PREVENT CONTAMINATION

(71) Applicant: Roche Molecular Systems, Inc., Pleasanton, CA (US)

(72) Inventors: Renato Belz, Rothenburg (CH); Christian Thalmann, Kehrsiten (CH)

(73) Assignee: Roche Molecular Systems, Inc., Pleasanton, CA (US)

( * ) Notice: Subject to any disclaimer, the term of this patent is extended or adjusted under 35 U.S.C. 154(b) by 940 days.

(21) Appl. No.: 13/715,700

(22) Filed: Dec. 14, 2012

(65) Prior Publication Data

US 2013/0164853 A1   Jun. 27, 2013

(30) Foreign Application Priority Data

Dec. 21, 2011   (EP) .................................... 11194991

(51) Int. Cl.
| | |
|---|---|
| *B01L 9/00* | (2006.01) |
| *G01N 35/10* | (2006.01) |
| *G01N 33/50* | (2006.01) |
| *G01N 35/00* | (2006.01) |

(52) U.S. Cl.
CPC .......... *G01N 35/1065* (2013.01); *B01L 9/543* (2013.01); *G01N 33/50* (2013.01); *B01L 2200/141* (2013.01); *G01N 2035/00277* (2013.01); *G01N 2035/103* (2013.01); *Y10T 436/11* (2015.01)

(58) Field of Classification Search
None
See application file for complete search history.

(56) References Cited

U.S. PATENT DOCUMENTS

| | | | |
|---|---|---|---|
| 6,182,719 B1 * | 2/2001 | Yahiro | B01L 9/543 141/1 |
| 2003/0072684 A1 | 4/2003 | Anderson et al. | |
| 2010/0284864 A1 | 11/2010 | Holenstein et al. | |
| 2011/0300620 A1 * | 12/2011 | Belz | B01L 3/50851 435/287.2 |

FOREIGN PATENT DOCUMENTS

| | | |
|---|---|---|
| EP | 1081234 A2 | 3/2001 |
| EP | 1081234 A3 | 4/2005 |
| EP | 1683577 B1 | 9/2009 |
| GB | 2452628 A | 3/2009 |
| JP | 2011123065 A | 6/2011 |

* cited by examiner

*Primary Examiner* — Lyle Alexander
*Assistant Examiner* — Michelle Adams
(74) *Attorney, Agent, or Firm* — Pamela C. Ancona; David J. Chang; M. Reza Savari (57) ABSTRACT

A method is provided for disposing of a liquid within an automated analytical system for processing a fluid biological sample, wherein a contamination prevention shield including channels for pipets or pipet tips is reversibly docked to a container for liquid waste in order to reduce the risk of cross-contamination. A tip rack assembly is provided for processing a fluid sample, the assembly including a rack for pipet tips and the contamination prevention shield. An analytical system is provided using the tip rack assembly, wherein cross-contamination is avoided.

9 Claims, 10 Drawing Sheets

ANALYTICAL SYSTEM WITH TIP RACK ASSEMBLY CONFIGURED TO PREVENT CONTAMINATION

CROSS-REFERENCES TO RELATED APPLICATIONS

The present application claims the benefit of priority under 35 U.S.C. §119 of EP 11194991.3, filed Dec. 21, 2011, the content of which is incorporated by reference herein in its entirety.

FIELD OF THE INVENTION

The present invention relates to the field of processing fluid biological samples for analytical purposes. In particular, the present invention relates to a method for disposing of a liquid within an automated analytical system for processing a fluid biological sample. The invention also provides a tip rack assembly for processing a fluid sample, said assembly comprising a rack for pipet tips and a contamination prevention shield. The invention further provides an analytical system using said tip rack assembly, wherein the risk of cross-contamination is reduced.

BACKGROUND OF THE INVENTION

The processing of biological materials is of considerable significance for analytical purposes.

Automated liquid handling devices are commonly used in such processes. Devices are commercially available which may include an automated pipet head assembly movable within the device so that it may be aligned with test tubes or vials for reagent liquid handling.

In some automated liquid handling devices, a pipet head assembly uses disposable pipet tips to aspirate and release samples and reagents. Aspiration and release may be performed according to protocols operated by a dedicated microcomputer. A work surface assembly may be provided which comprises various elements to enable positioning of pipet tips, reagent containers, sample containers and the like. A multiwell format is frequently adopted so that a number of parallel pipetting channels can be employed simultaneously to enable simultaneous processing of a number of samples.

When the automated liquid handling device processes samples, for example so as to purify a molecule from a complex mixture, one of the most striking challenges is that there should be no contamination between vessels such as, e.g., microwells containing one sample and vessels containing another sample. This is commonly referred to as cross-contamination.

Attempts have been made to address this problem, e.g., by a symmetrical setup of a work surface assembly in which the loaded pipets are not passed over unused vessels containing other reagents or samples, as described in GB 2452628.

Document EP 1081234 discloses a liquid waste container with separate sections for the introduction of multiple pipet tips in order to prevent cross-contamination when liquid waste is dispensed into a waste container.

The present invention provides a method for disposing of a liquid within an automated analytical system for processing a fluid biological sample, said method displaying several advantages.

SUMMARY OF THE INVENTION

In a first aspect, as set out supra, the invention relates to a method for disposing of a liquid within an automated analytical system for processing a fluid biological sample. During said processing, liquid waste is generated which is aspirated into pipets or pipet tips of a pipet array. After reversibly docking a contamination prevention shield comprising channels to a common liquid waste container, the liquid waste is discarded into said waste container by introducing the pipets or pipet tips of said pipet array or a part thereof into the channels of said contamination prevention shield, wherein said channels are geometrically prearranged for the introduction of the tips of said pipet array. Said channels form contamination barriers between said pipets or pipet tips, wherein each of said pipets or pipet tips or a part thereof is introduced into a different channel. The liquid waste or a part thereof is then dispensed into said common liquid waste container.

Another aspect of the invention provides a tip rack assembly comprising an upper part and a bottom part. The upper part includes a rack with multiple receptacles adapted for storing pipet tips, and the bottom part comprises a contamination prevention shield with multiple channels separated from each other in a fluid-proof manner. These channels are adapted for the introduction of said pipet tips. Said contamination prevention shield is fixed to said rack but can be removed therefrom.

In a further aspect, the invention relates to an analytical system for processing fluid biological samples, said system comprising the tip rack assembly as described above, a pipetting device comprising a pipet array, and a waste station comprising a liquid waste container. The liquid waste container is adapted for reversibly docking to said contamination prevention shield. The system further comprises a transferring device for transporting said tip rack assembly or its separated upper and/or bottom part between different units of said system.

BRIEF DESCRIPTION OF THE FIGURES

Other and further objects, features and advantages of the invention will appear more fully from the following description. The accompanying drawings, together with the general description given above and the detailed description given below, serve to explain the principles of the invention.

DETAILED DESCRIPTION OF THE INVENTION

By way of illustration, specific exemplary embodiments in which the invention may be practiced now are described. In this regard, terminology with respect to orientations and directions such as "horizontal", "vertical", "upper", "lower" is used with reference to the orientation of the figure being described. Because components described can be positioned in a number of different orientations, this terminology is used for the purpose of illustration only and is in no way limiting.

In one embodiment, a method is provided for disposing of a liquid within an automated analytical system, said method comprising the steps:

b. processing a fluid biological sample within said automated analytic system, wherein liquid waste is generated, c. reversibly docking a contamination prevention shield (4) comprising channels (14) to a common liquid waste container (7), d. aspirating said liquid waste or a part thereof into pipets or pipet tips (3) of a pipet array (13), e. introducing the pipets or pipet tips (3) of said pipet array (13) or a part thereof into the channels (14) of said contamination prevention shield (4), wherein said channels are geometrically prearranged for the introduction of the tips (3) of said pipet array (13), wherein said channels (14) form contamination barriers between said pipets or pipet tips (3) and wherein each of said pipets or pipet tips (3) or a part thereof is introduced into a different channel (14), f. dispensing said liquid waste or a part thereof through said channels (14) into said common liquid waste container (7), wherein step c. can be before, after or at the same time as step d.

When dealing with biological samples, it is crucial— especially in the field of in-vitro diagnostics—that cross-contamination is avoided to the largest possible extent. If, for example, biological material is accidentally transferred from one sample to another one, the consequences may be severe. For instance, if said samples are clinical samples derived from different individuals, then a positive diagnostic result might be yielded for both samples and thus individuals even though only one of the samples contains a certain pathogen.

Such "false-positive" results can cause the initiation of unnecessary treatment, and in the case of many drugs the patient is exposed to unpleasant or even threatening side effects. Besides, many therapies are rather costly, putting a superfluous burden on patient and/or health insurance, and possibly leading to unnecessary hospital stays in the cases of stationary treatment.

The risk of creating false-positive results due to cross-contamination is especially imminent when dealing with methods involving the amplification of the biological material to be isolated and analyzed. For instance, the analysis of nucleic acids often involves amplification methods such as the Polymerase Chain Reaction (PCR), where even minute amounts of specific nucleic acids can be detected. In turn, such high sensitivity also implies that very low amounts of a contaminant (such as, e.g., a nucleic acid from a different sample) can be detected and analyzed.

The method disclosed in EP 1081234 aims at the reduction of the risk of cross-contamination between different pipets or their tips, respectively. It discloses a liquid waste container with several separated sections for different pipet tips. While cross-contamination is avoided, some structures of the liquid waste container get in contact with the disposed waste of the respective pipetting event. Especially in the case of medium to high throughput analyses and/or "sip-and-spit" mixing concepts, it is desirable to reuse disposable elements such as, e.g., pipet tips. However, if a liquid waste container as described in the prior art has been used several times, the risk of cross-contamination increases with each pipetting event.

Embodiments of the present invention provide an advantageous method to avoid such cross-contamination without the need of frequently replacing pipet tips or even the entire waste container.

By reversibly docking a contamination prevention shield (4) comprising channels (14) to a common liquid waste container (7), said shield (4) can be readily removed after a certain number of uses and replaced by a fresh one.

Thus, pipet tips can be reused several times, thereby reducing costs and producing smaller amounts of solid waste. Besides, the time-to-result is shortened by reducing the steps of attaching and releasing pipet tips.

For instance, if different fluid samples are contained within a plurality of vessels, then specific pipet tips (3) of a pipet array (13) may be used for specific samples, wherein a specific pipet tip (3) can be used multiple times on the respective sample, since the risk of cross-contamination between the different specific pipet tips (3) and thus samples is reduced in the method described above. One example for the multiple reuse of a pipet tip (3) on a given sample is the performance of multiple washing steps, wherein mixing is carried out by aspirating and releasing the liquid with the respective pipet tip (3).

The method according to embodiments of the invention is also advantageous as compared with a possible exchange of the entire liquid waste container. Handling a container within an analytical system such as an apparatus comprising a housing is more complex and prone to contamination than handling only a comparatively small removable part such as the contamination prevention shield (4). Replacing the whole container is further more costly than the method according to embodiments of the invention and creates more solid waste.

By using the removable contamination prevention shield (4) according to an embodiment of the present invention, only the part of the liquid waste container arrangement is replaced that comes into contact with sample material, thus providing a more practical and less cost- and time-intensive method.

In certain embodiments, the present invention enables the skilled person to separate liquid from solid waste. This bears the advantage of a further reduced risk of contamination since liquid waste is mostly easier to handle, it can, e.g., be pooled and sealed prior to removing it from the system. Solid waste, on the other hand, tends to be more bulky and is usually not comprised in a closed container for disposal. Thus, a mixture of liquid and solid waste, e.g., in the case of the removal of a disposable waste container filled with liquid waste, often causes an increased contamination risk. For instance, the liquid waste could be spilled from the container when moving the latter through the system in order to dispose of it.

According to some embodiments, the liquid waste can, e.g., be aspirated from the liquid waste container (7) into pipets or pipet tips (3). If the contamination prevention shield (4) is still docked to the liquid waste container (7), the risk of contamination of the system is further reduced. The shield (4) can then be disposed of separately. However, it is also within the scope of certain embodiments of the invention that the shield (4) is removed from the container (7) first and the liquid waste is withdrawn from the container (7) thereafter, or at a later point in time.

In the context of the embodiments of the present invention, the terms "isolation", "purification" or "extraction" of biological material relate to the following: Before biological materials like nucleic acids may be analyzed in a diagnostic assay, e.g., by amplification, they typically have to be purified, isolated or extracted from biological samples containing complex mixtures of different components. Suitable methods are known to the person skilled in the art.

Typically, one of the first steps comprises releasing the contents of cells or viral particles, e.g., by using enzymes and/or chemical reagents. This process is commonly referred to as lysis. For enrichment of the analyte in question in the lysate, one useful procedure for binding nucleic adds entails the selective binding of nucleic acids to glass surfaces of binding particles such as, e.g., magnetic particles in chaotropic salt solutions and separating the nucleic acids from contaminants such as agarose, proteins or cell debris. In some embodiments, the glass of the particles is formed using the gel sol process described in WO 96/41811 and then dried and compressed.

"Biological material", in the sense of the embodiments of the invention, comprises all kinds of biological molecules, for example proteins or nucleic acids, but also other molecules occurring in nature or being derivatives or synthetic analogues or variants thereof. Furthermore, the term "biological material" comprises viruses and eukaryotic and prokaryotic cells.

A "fluid sample" is any fluid material that can be subjected to a diagnostic assay and is in some embodiments derived from a biological source. In some embodiments, said fluid sample is derived from a human and is a body liquid. In an embodiment of the invention, the fluid sample is human blood or blood plasma, urine, sputum, sweat, swab, pipettable stool, or spinal fluid. In other embodiments, the fluid sample is human blood or blood plasma.

"Reversibly docking" in the sense of the embodiments of the invention means attaching objects to each other with the possibility of subsequent or later undocking. For instance, a contamination prevention shield (4) can be reversibly docked to a liquid waste container (7) by any suitable mechanism such as, e.g., latches, force fit (e.g., by friction/sticky surfaces), form fit (e.g., bolting, bayonet coupling, snap fitting, an undercut in the casting), hook-and-loop fastening, pressure (e.g., exerted by a pipetting head, or applying a vacuum), magnetism, or other means. "Reversibly docking" implies that the undocking can be easily carried out without destroying or damaging any of the involved objects.

"Contamination prevention shield" means a device that is suitable for reducing the risk of cross-contamination during pipetting, especially in the context of liquid waste disposal. According to embodiments of the invention, said contamination prevention shield (4) comprises channels (14) and reduces the risk of cross-contamination between fluid material that is passed through distinct of said channels (14) by pipets or pipet tips (3). The channels (14) are separated from each other in a manner not allowing for any material in a certain channel to contaminate a different channel (14) and/or the fluid material or pipet or pipet tip (3) therein. Each channel (14) has dimensions in which only one pipet or pipet tip (3) can be introduced, so that each pipet or pipet tip (3) is introduced in a different channel (14). In some embodiments, the contamination prevention shield (4) has structures for the interaction with a handling device, suitable structures being, e.g., recesses, latches, protrusions or others. Also in some embodiments, the contamination prevention shield (4) has structural elements allowing the reversible docking to the liquid waste container (7) as described supra.

A "liquid waste container" is a container for collecting liquid that is no longer needed in an isolation or analytic process. Such a container (7) can be made from different materials, comprising, e.g., metal or plastics. If, for example, the container (7) is made of plastic, its production process in some embodiments includes injection molding, such that, e.g., fastenings may be introduced during the production steps. The container (7) is in some embodiments made of polypropylene. As known to the person skilled in the art, a suitable molding tool is used for production of the liquid waste container (7).

The "waste station" is the part that comprises the liquid waste container (7) within an automated analytical system. In the context of the invention, said waste station may comprise other elements, such as, e.g., a holder for mounting the liquid waste container (7). The waste station can, e.g., also comprise a means to withdraw the liquid waste from the liquid waste container (7) through the bottom of said container (7).

In the context of embodiments of the invention, a "pipet array" means an assembly of multiple pipets or pipetting needles, such as for example a multichannel pipet. In some embodiments, the pipet array (13) contains an upper part that is attached to a holder, and a lower part comprising one or more pipets or pipetting needles. In some embodiments the pipet array (13) comprises pipetting needles. In the case of a pipet, said pipet in some embodiments comprises one or more disposable pipet tips (3) into which said suspension is aspirated and from which it is dispensed again. Such pipet tips (3) can be used several times before being discarded and replaced. Disposable pipet tips (3) useful for the invention in some embodiments have a volume of at least 10 µl, or at least 15 µl, or at least 100 µl, or at least 500 µl, or at least 1 ml, or about 1 ml.

"Geometrically prearranged" in the context of the channels (14) of said contamination prevention shield (4) means that said channels (14) or at least a part thereof are arranged relative to each other corresponding to the relative arrangement among said pipets or pipet tips (3), such that, e.g., the different pipets or pipet tips (3) of said pipet array (13) can be introduced into the corresponding channels (14) of said contamination prevention shield (4) at the same time. For instance, in the case of a multichannel pipet with eight pipets or pipet tips (3) arranged in a row, respectively, the geometrically prearranged channels (14) of said contamination prevention shield (4) would also be at least eight arranged in a row as well, so that all eight pipets or pipet tips (3) of said array (13) could be introduced into said channels (14) at the same time. In an embodiment, the number of geometrically prearranged channels (14) corresponds to the number of pipets or pipet tips (3). In another embodiment, the total number of geometrically prearranged channels (14) is a multiple of the number of the pipets or pipet tips (3) of said pipet array (13). In an embodiment, the channels (14) are geometrically prearranged in columns and rows, which are in some embodiments perpendicular to each other. Also in some embodiments, the number of channels (14) within a column or a row corresponds to the number of the pipets or pipet tips (3) of said pipet array (13). In some embodiments, the pipets or pipet tips (3) of said array (13) are introduced into one column or row of channels (14) of said contamination prevention shield (4) at one pipetting event and into a different column or row at another pipetting event. In some embodiments, each channel (14) is used only once. In other embodiments, the contamination prevention shield (4) has 12, 24, 48 or 96 channels. In some embodiments, said channels (14) are arranged in columns and rows in a 3×4, 4×6, 6×8 or 8×12 arrangement.

"Geometrically prearranged" in the context of said channels (14) also means that each channel (14) is structurally adapted for the introduction of a pipet or pipet tip (3) of said pipet array (13). The channels (14) are constructed in a manner such that the pipets or pipet tips (3) do not reach the outlet openings of the channels (14). When inserted into the channels, the outlet openings of said pipets or pipet tips (3) are located within said channels (14), such that any liquid dispensed from said pipets or pipet tips (3) is dispensed within the respective channels, thus reducing the risk of cross-contamination between the different pipets or pipet tips (3). In some embodiments, the outlet opening of the channel (14) has a smaller diameter than the corresponding inlet opening. Also in some embodiments, the channels (14) are essentially conical with the outlet opening of the channel (14) being the narrow end of the cone. Also in some embodiments, the introduced pipet or pipet tip (3) leaves no space between its own outer diameter and the inner diameter of a certain point of the channel (14), such that liquid or gas essentially only passes through said channel (14) via said introduced pipet or pipet tip (3).

"Contamination barrier" means a structure that prevents a potential contaminant from spreading from one compartment to another one. In the context of embodiments of the invention, the channels (14) of said contamination prevention shield (4) form such contamination barriers, since the channels (14) are spatially separated from each other such that the content or flowthrough of a given channel (14) does not contaminate a different channel.

Embodiments of the present invention are especially advantageous when applied in connection with disposable pipet tips (3). The embodiments of the present invention allow for the multiple use of disposable pipet tips (3) while reducing the risk of cross-contamination and reducing the amount of pipet tip waste at the same time.

Hence, an aspect of the invention is the method described above, wherein said tips are disposable pipet tips (3).

In some embodiments of the invention, said contamination prevention shield (4) is provided in connection with a tip rack (2) comprising disposable pipet tips (3). These embodiments permit the introduction of both the contamination prevention shield (4) and the rack (2) comprising disposable tips (3) into the system at the same time without a separate handling process for each single component. It is advantageous to provide said tip rack (2) and said shield (4) together, e.g., in embodiments comprising disposable pipet tips (3), where waste is only produced when disposable pipet tips (3) are available, such that then the presence of the contamination prevention shield (4) is required. Furthermore, providing these two components together bears the advantage of reduced packaging material and a simplified workflow for the skilled person, since he only needs to introduce one combined object into the analytical system instead of two separate ones. It is important that the connection between said rack (2) and said shield (4) is not permanent, but can be released without destroying or otherwise rendering inoperative any of these two components.

Summarizing, an aspect of the invention is the method described above, wherein said disposable pipet tips (3) are retrieved from a tip rack assembly (1), said tip rack assembly (1) comprising
a tip rack (2) comprising said disposable pipet tips (3),
said contamination prevention shield (4),
wherein said contamination prevention shield (4) is removably fixed to said tip rack (2) and released therefrom in step c.

In the context of embodiments of the invention, "removably fixed" means that an object is attached to another object with the ability to be removed from it again, be it in a reversible manner or not. For instance, while the term "removably fixed" or "removably fixing" comprises the meaning of "reversibly docked" or "reversibly docking" (see supra), it further comprises the possibility that an object can only be removed once from the other object, but cannot be reattached thereafter, e.g., because the fixing element or elements are destroyed during removal. However, as in "reversibly docking", even if fixing elements are destroyed upon separation of the components, the latter still remain functional with regard to their respective purposes, e.g., as a tip rack (2) or as a contamination prevention shield (4).

Suitable mechanisms for "removably fixing" comprise, in principle, the same mechanisms as for "reversible docking", but in some cases also structures that are irreversibly destroyed upon removal as set out above, such as, e.g., heat-sealing or gluing.

In an embodiment of the method described supra, said contamination prevention shield (4) is reversibly docked to said tip rack (2). In such an embodiment, the shield (4) can be reattached to the tip rack (2), which can, e.g., be advantageous when discarding rack (2) and shield (4) together.

Advantages of embodiments where the contamination prevention shield (4) is comprised by said tip rack assembly (1) are, for example, that the skilled person only needs to acquire, transport and handle a single element, which is in some embodiments a disposable element. Furthermore, only one element needs to be introduced into the analytical system instead of two separate ones. Such an integrated solution is thus advantageous in terms of costs, logistics and practical use.

As described supra, it is advantageous that according to embodiments of the invention the contamination prevention shield (4) can be detached from the liquid waste container (7) for the reasons mentioned above.

Thus, an aspect of the invention is the method described above, further comprising the step of releasing said contamination prevention shield (4) from said common liquid waste container (7) after step f. and discarding it.

In this embodiment, the contamination prevention shield (4) can be used once or several times. In some embodiments, the contamination prevention shield (4) comprises more channels (14) than the pipet array (13) contains pipets or pipet tips (3), such that in some embodiments each channel (14) is only used once as described above before the shield (4) is removed from the liquid waste container (7) and discarded. In some embodiments, the contamination prevention shield (4) is replaced by a fresh one which has not been used before.

The method according to embodiments of the invention is particularly, while not only, useful in medium- to high-throughput systems. Multiple samples and/or replicates of a sample can be processed simultaneously in a plurality of vessels, while disposable material such as, e.g., disposable pipet tips can be used several times, while techniques like mixing solutions or suspensions by single or repeated aspirating and dispensing can be advantageously applied.

The terms "vessel", "receiving vessel" or "reaction vessel" comprise, but are not limited to, tubes or the wells of plates such as microwell, deepwell or other types of multi-well plates, in which a reaction for the analysis of the fluid sample such as, e.g., reverse transcription or a polymerase chain reaction takes place. The outer limits or walls of such vessels are chemically inert such that they do not interfere with the analytical reaction taking place within.

In the case of multiple vessels, for the ease of handling and to facilitate automation, in some embodiments the vessels are combined in an integral arrangement, so they can be manipulated together.

Consequently, an aspect of the invention is the method described above, wherein multiple vessels are combined in an integral arrangement.

Integral arrangements can, e.g., be vials or tubes reversibly or irreversibly attached to each other or arranged in a rack. In some embodiments, the integral arrangement is a multiwell plate. In some embodiments, the multiwell plate is a deepwell plate.

In the case of simultaneous processing of multiple different samples while possibly also using multiple different reagents, an advantage of the present invention is that these can be processed in separate pipets with a reduced risk of contamination, while retaining the advantage of parallel processing.

Thus, an aspect of the invention is the method described above, wherein each pipet or pipet tip (3) of said pipet array (13) contains a different reagent or sample.

In some embodiments of the method described above, the analyte is a nucleic acid.

Also an aspect of the invention is the method described above, further comprising after the last step amplifying and analyzing said nucleic acid.

In some embodiments of the method described above, said amplification and analysis is carried out by PCR.

The PCR (Polymerase Chain Reaction) is a well-known method in the art and is disclosed, among other references, in U.S. Pat. Nos. 4,683,202, 4,683,195, 4,800,159, and 4,965,188.

Other nucleic acid amplification methods to be used in the context of the invention comprise the Ligase Chain Reaction, Polymerase Ligase Chain Reaction, Repair Chain Reaction, NASBA, strand displacement amplification (SDA), transcription mediated amplification (TMA), and Qb-amplification. Such amplification methods are known to the person skilled in the art.

In view of the embodiments of the method described above involving the tip rack assembly (1), the latter is also an aspect of the invention.

In detail, said aspect is a tip rack assembly (1) comprising
an upper part comprising a rack (2) with multiple receptacles (20, 21) adapted for storing pipet tips (3),
a bottom part comprising a contamination prevention shield (4) with channels (14), wherein said channels (14) are geometrically prearranged for the introduction of said pipet tips (3), and wherein said channels (14) form contamination barriers between said pipet tips (3),
wherein said contamination prevention shield (4) is removably fixed to said rack (2).

As set out above, such a tip rack assembly (1) abolishes the need to introduce both the tip rack (2) and the contamination prevention shield (4) independently from each other, thus reducing costs for packaging and also reducing the respective solid waste, as well as reducing the number of required handling steps.

Said removable fixing can be realized in a number of different ways as described supra. In some embodiments of the tip rack assembly (1) of the invention, the contamination prevention shield (4) is removably fixed to said rack (2) via one or more latches.

The tip rack (2) is particularly useful when used in connection with disposable pipet tips (3), as described above.

Thus, an aspect of the invention is the tip rack assembly (1) described above, wherein a part or all of the multiple receptacles (20, 21) of said rack (2) contain disposable pipet tips (3).

A possible production method for the tip rack assembly (1) described above is depicted in FIG. 26.

In line with the embodiments described above in the context of the method of the present invention, it is useful to provide at least one channel (14) for each pipet or pipet tip (3), while a given channel (14) is only used for a specific pipet or pipet tip (3).

Hence, an aspect of the present invention is the tip rack assembly (1) described above, wherein said channels (14) are geometrically arranged such that a channel (14) is provided for each of said multiple pipet tips (3) attached to a multichannel pipettor (13).

The use of a multichannel pipettor is furthermore advantageous in view of increased throughput and simultaneous processing of multiple different samples possibly using multiple different reagents.

Furthermore, it is advantageous if said channels (14) provide guidance for the introduced pipets or pipet tips (3). In this context, said channels (14) have specific forms. For instance, in some embodiments, the outlet opening of the channel (14) has a smaller diameter than the corresponding inlet opening. Also in some embodiments, the channels (14) are essentially conical with the outlet opening of the channel being the narrow end of the cone. Also in some embodiments, the introduced pipet or pipet tip (3) leaves no space between its own outer diameter and the inner diameter of a certain point of the channel (14), such that liquid or gas only passes through said channel (14) via said introduced pipet or pipet tip (3). This bears the advantage, among others, that the liquid waste present in the liquid waste container (7) after a certain number of liquid waste disposal events can be efficiently emptied using the pipets and/or pipet tips of said pipetting array, or other pipets and/or pipet tips (3). In some embodiments, the liquid waste container (7) with the reversibly docked contamination prevention shield (4) does not have other openings than said channels (14). In these embodiments, the efficiency of withdrawing the liquid waste from the liquid waste container (7) for removing it from the analytical system is further enhanced, since no liquid or gas can pass the walls of the liquid waste container (7) elsewhere than through said channels (14).

An aspect of the invention is the tip rack assembly (1) described supra, wherein each of said channels (14) forms a funnel (15) for centering each of said pipet tips (3) within said channels (14).

In this embodiment, the above-mentioned advantages are achieved, i.e. the pipet tips (3) are guided within the channels (14), cross-contamination is reduced, and the efficiency of emptying the liquid waste container (7) using pipets is increased. Moreover, such embodiments prevent the formation of drops or foam at the pipet tips (3) after pipetting events or after emptying the liquid waste container (7), such that the pipet array (13) can be handled within the system with a reduced risk of contamination due to dripping of liquid or foam. In some embodiments, the dispensation of the liquid waste into the liquid waste container (7) is performed in the form of a jet. If the liquid waste leaves the pipet or pipet tip (3) as a jet, capillary action is diminished that could potentially promote retaining drops or foam at the pipet or pipet tip (3).

Also an aspect of the present invention is an analytical system for processing fluid biological samples, said system comprising
  the tip rack assembly (1) described supra
  a pipetting device comprising a pipet array (13)
  a waste station comprising a liquid waste container (7), wherein said liquid waste container (7) is adapted for reversibly docking to said contamination prevention shield (4)
  a transferring device for transporting said tip rack assembly (1) or its separated upper and/or bottom part between different units of said system.

The "pipetting device comprising a pipet array" is a tool that accomplishes aspirating and dispensing, e.g., reagents or samples, and thus transferring them between the other different components of said system. The pipetting device can comprise, e.g., a robotic device with a movable robotic arm. Within an automated system, a pipetting device often comprises an actuator such as a motor, allowing for precise and reproducible movements.

The "transferring device" is a device for transporting system components within the analytical system. For instance, the transferring device can be a robotic arm with a gripper or another suitable device.

Another aspect of the invention is the analytical system described above, further comprising one or more elements selected from the group consisting of:
  a reaction module containing the components of a chemical and/or biochemical reaction
  a detection module for detecting signals evoked by an analyte
  a storage module for reagents and/or disposables.

A "reaction module" is a module in which a reaction such as, e.g., a Polymerase Chain Reaction (PCR) or hybridization of antibodies for the analysis of the sample or a specific analyte therein takes place. It can, e.g., comprise a variety of vessels like tubes or plates. The outer limits or walls of such vessels are chemically inert such that they do not interfere with the analytical reaction taking place within.

A "detection module" is a module in which the detection of a signal, in some embodiments the signal evoked by an analyte or a control, is performed. A detection module can, e.g., be an optical detection unit for detecting the result or the effect of the analysis procedure. An optical detection unit may comprise a light source, e.g., a xenon lamp, optics such as mirrors, lenses, optical filters, fiber optics for guiding and filtering the light, one or more reference channels, or a CCD camera.

A "storage module" stores the necessary reagents to bring about isolation of biological material and/or a chemical or biological reaction important for analysis of the sample in question. It can also contain further components useful for the method of the invention, e.g., disposables such as pipet tips or vessels to be used as reaction receptacles within the reaction module.

In some embodiments, the analytical system according to the invention further comprises a control unit for controlling system components.

A control unit may comprise software for ensuring that the different components of an analytical system work and interact correctly and with the correct timing, e.g., moving components such as, e.g., the pipetting device comprising a pipettor in a coordinated manner. The control unit may also comprise a processor running a real-time operating system (RTOS), which is a multitasking operating system intended for real-time applications. In other words the system processor is capable of managing real-time constraints, i.e. operational deadlines from event to system response regardless of system load. It controls in real time that different units within the system operate and respond correctly according to given instructions.

Another aspect of the invention is the analytical system described above, wherein the liquid waste container (7) comprises a mechanism to release the contamination prevention shield (4) from the rack (2) of the tip rack assembly (1) and/or to dock the contamination prevention shield (4) to the liquid waste container (7).

In some embodiments of the invention, said mechanism of said analytical system comprises one or more conical pins (8) and/or one or more latches.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

DETAILED DESCRIPTION OF THE FIGURES

In the following, specific embodiments of the invention are disclosed in more detail. It has to be understood that these embodiments are not limiting with regard to the invention.

Figure 1:
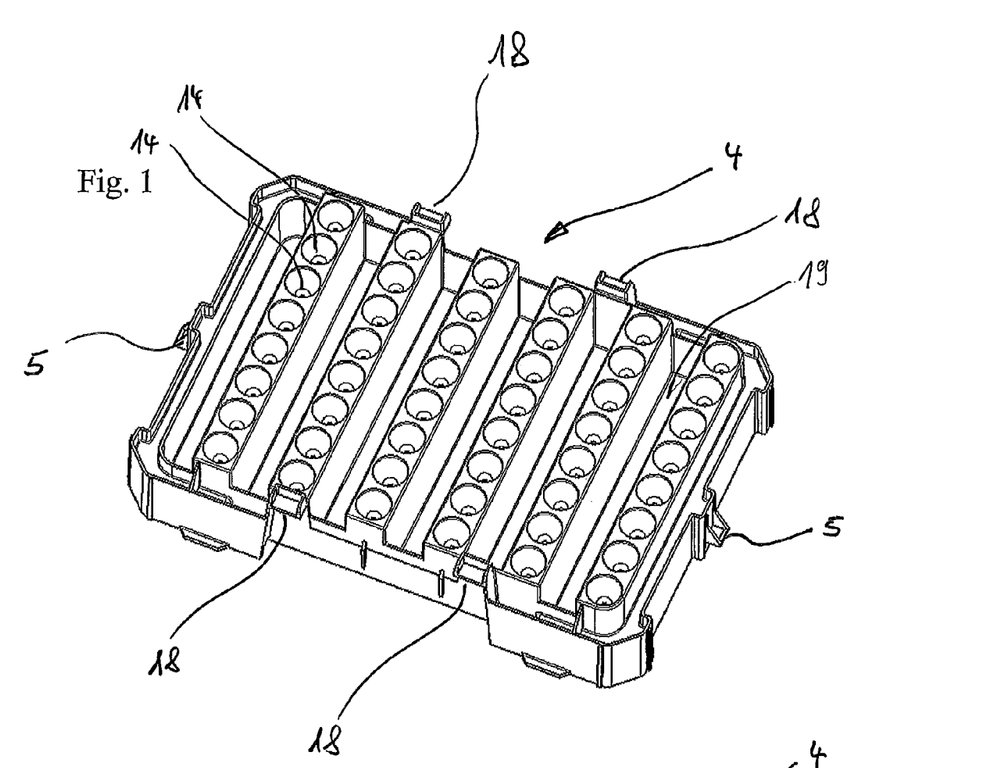
FIG. 1 shows a perspective view of a contamination prevention shield (4) from above.

FIG. 1 shows a perspective view of a separate contamination prevention shield (4) comprising channels (14). In the depicted embodiment, said contamination prevention shield (4) further comprises snap-fits (5) for removably fixing the shield (4) to a tip rack (2). Moreover, the depicted shield (4) has fits (18) for a handling or transferring device such as a gripper. Between said channels (14), there are cavities (19) which further reduce the risk of cross-contamination between the channels (14) and thus the pipets or pipet tips (3) to be introduced therein.

Figure 2:
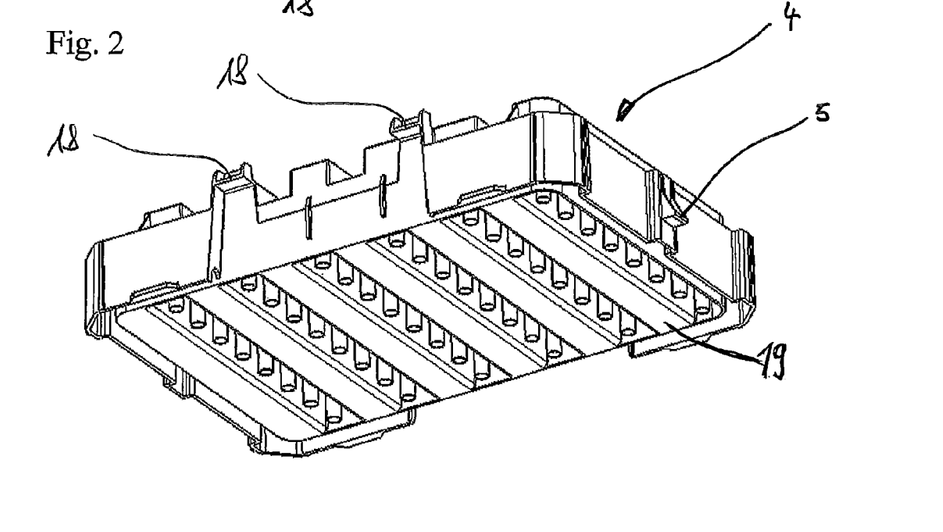
FIG. 2 shows a perspective view of a contamination prevention shield (4) from below.

FIG. 2 shows the same elements as FIG. 1, however as seen from below.

Figure 3:
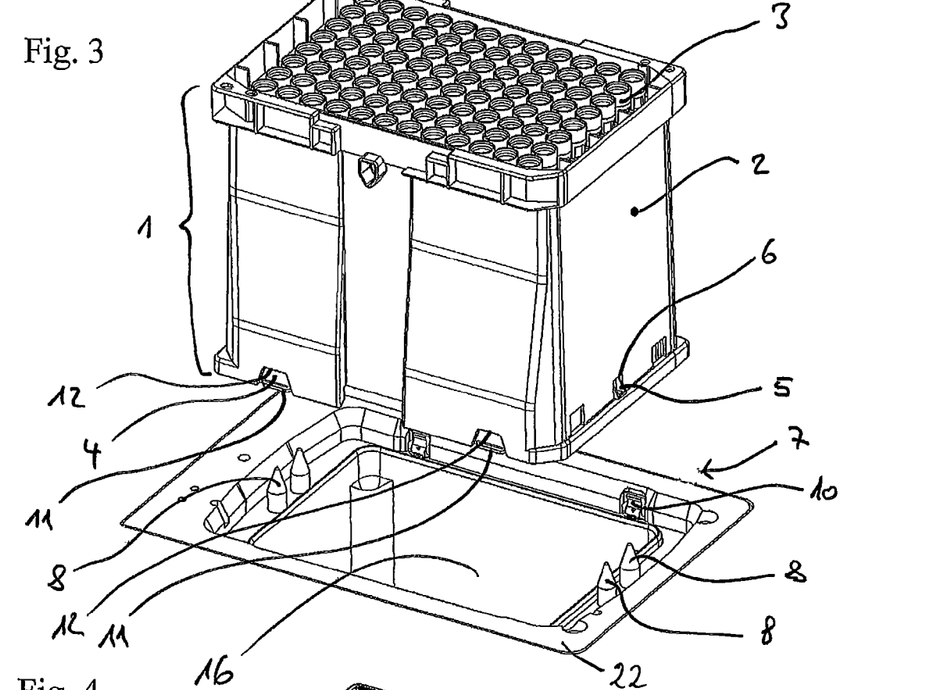
FIG. 3 shows a perspective view of a tip rack assembly (1) from above, situated above a liquid waste container (7).
Figure 4:
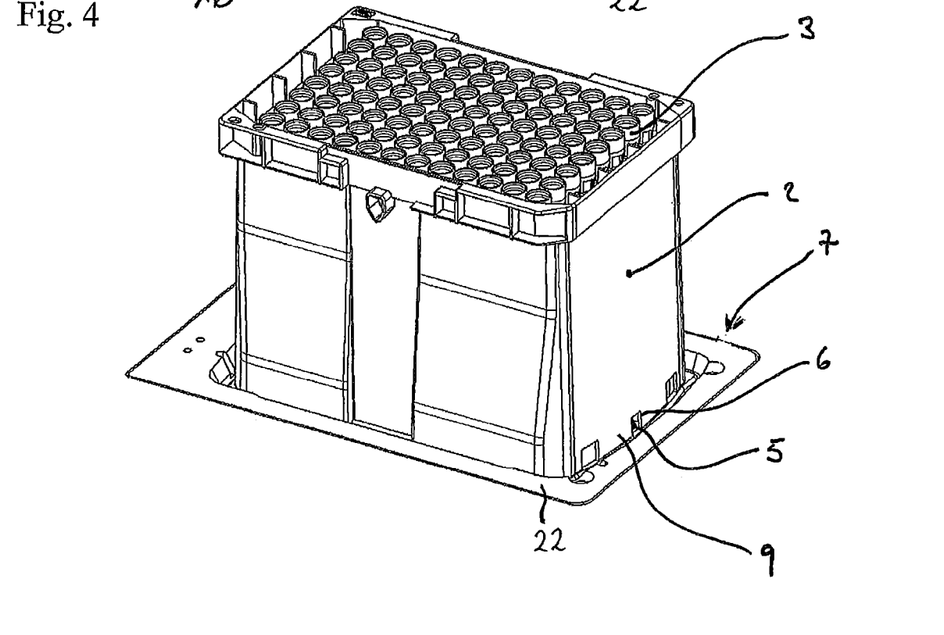
FIG. 4 shows a perspective view of a tip rack assembly (1) from above, docked onto the liquid waste container (7).
Figure 5:
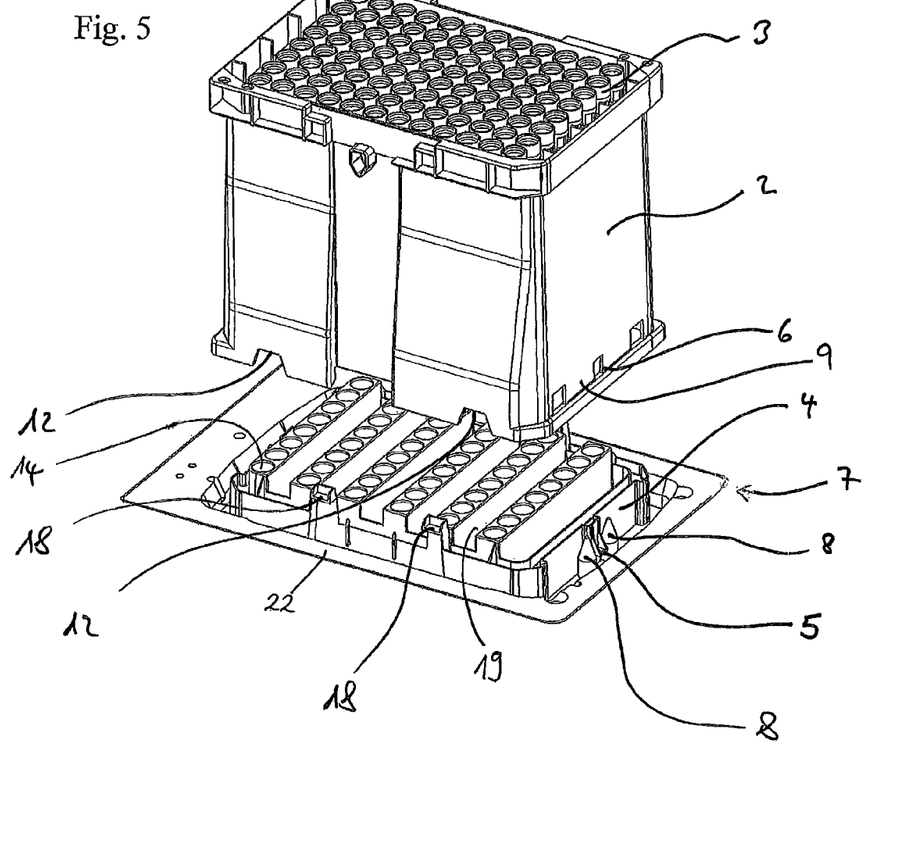
FIG. 5 shows a perspective view of a tip rack assembly (1) from above, situated above a liquid waste container (7), after docking the contamination prevention shield (4) to the liquid waste container (7).

FIGS. 3 to 5 show the process of reversibly docking a contamination prevention shield (4) from a tip rack assembly (1) to a liquid waste container (7) as a sequence of steps:

FIG. 3: The contamination prevention shield (4) is largely concealed by the tip rack (2), to which it is removably fixed by hooking the snap-fits (5) described above into corresponding recesses (6) of said tip rack (2), thus forming a tip rack assembly (1). In this depiction, the tip rack assembly (1) comprising pipet tips (3) is moved towards the opening of a liquid waste container (7). The current figure shows the rim (22) of the opening of said liquid waste container (7) framing the liquid waste-receiving inner space (16) of the latter. Said rim (22) comprises conical pins (8) as well as holding-down clamps (10) for interaction with the tip rack assembly (3). Said holding-down clamps (10) are arranged to hold down the mounting links (11) of the contamination prevention shield (4). In order to prevent the undesired interaction between clamps (10) and the walls of the tip rack (2), the latter contain cut-outs (12).

FIG. 4 shows the tip rack assembly (1) while releasing the contamination prevention shield (4) and thereby reversibly docking the latter to the liquid waste container (7). The conical pins (8, concealed) extend the shorter side walls (9) of the tip rack (2) around the recesses (6), such that the snap-fit connection between the snap-fits (5) and the recesses (6) is released. A more detailed depiction of this mechanism is provided in FIG. 11 or 15, respectively.

FIG. 5: The upper part of the tip rack assembly comprising the tip rack (2) has been removed from the liquid waste container (7) in this figure. The contamination prevention shield (4) is now reversibly docked to the liquid waste container (7).

Figure 6:
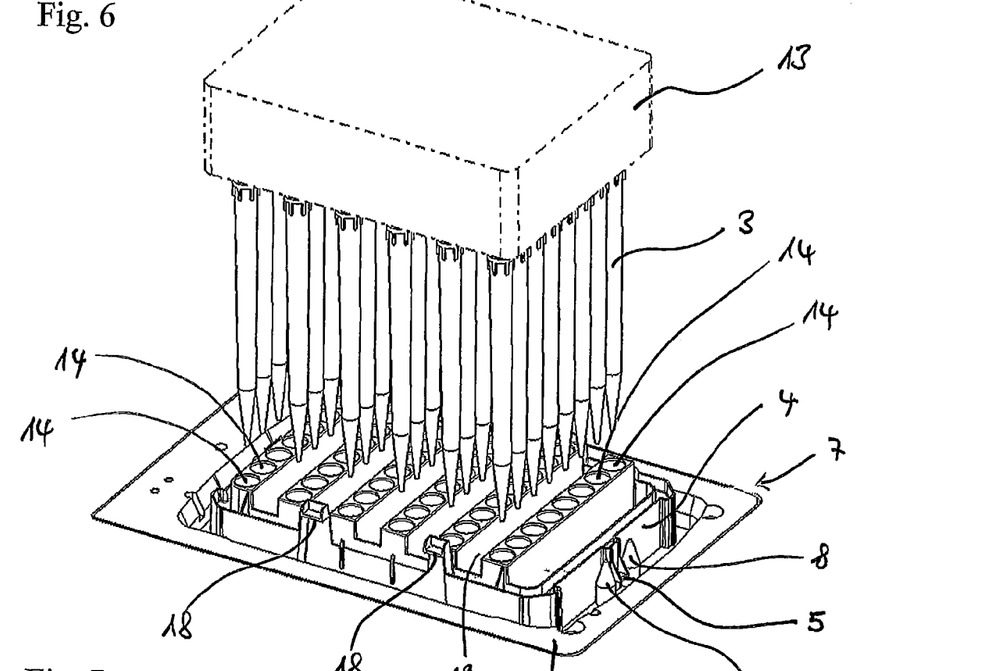
FIG. 6 shows a perspective view of a multichannel pipettor (13) comprising pipet tips (3) above a process liquid waste container (7) with a docked contamination prevention shield (4).

FIGS. 6 to 9 show, in a perspective view, the process of introducing the pipet tips (3) of a pipet array (13) into the channels (14) of a contamination prevention shield (4) in order to dispose of liquid waste from said tips (3) through the shield (4) into the inner space (16) of the liquid waste container (7):

FIG. 6: A pipet array (13), in this embodiment a pipetting head of an automated pipetting device, bears a plurality of pipet tips (3) that are about to be introduced vertically into the channels (14) of the contamination prevention shield (4). In this depiction, said pipetting head (13) comprising said tips (3) has been moved centrically above the channels (14) of the contamination prevention shield (4).

Figure 7:
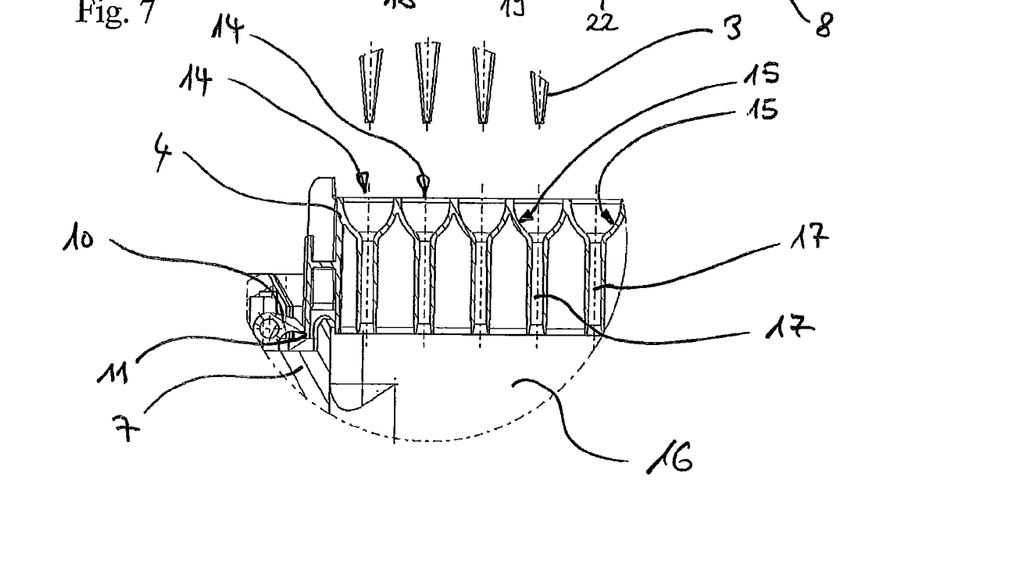
FIG. 7 shows a cross-section view of the contamination prevention shield (4) in the setup of FIG. 6, multichannel pipettor (13) comprising pipet tips (3) above a liquid waste container (7) with a reversibly docked contamination prevention shield (4).

FIG. 7: This closed-up cross-section of the process waste insert (4) in the setup of FIG. 6 shows the pipet tips (3) above the channels (14). The channels (14) in this embodiment comprise an upper part forming an intake guide (15) for the pipet tips (3) to be introduced into the channels (14). The latter further comprise a lower part forming the actual flow-through channel (17), the diameter of which does not allow the complete passage of a pipet tip (3). The channels (14) facilitate the passage of the liquid waste from the pipet tips (3) into the inner space (16) of the liquid waste container (7).

The figure further shows the reversible docking mechanism of the contamination prevention shield (4) to the liquid waste container (7) via the holding-down clamps (10) of the liquid waste container (7), said clamps (10) holding down the mounting links (11) of the contamination prevention shield (4).

Figure 8:
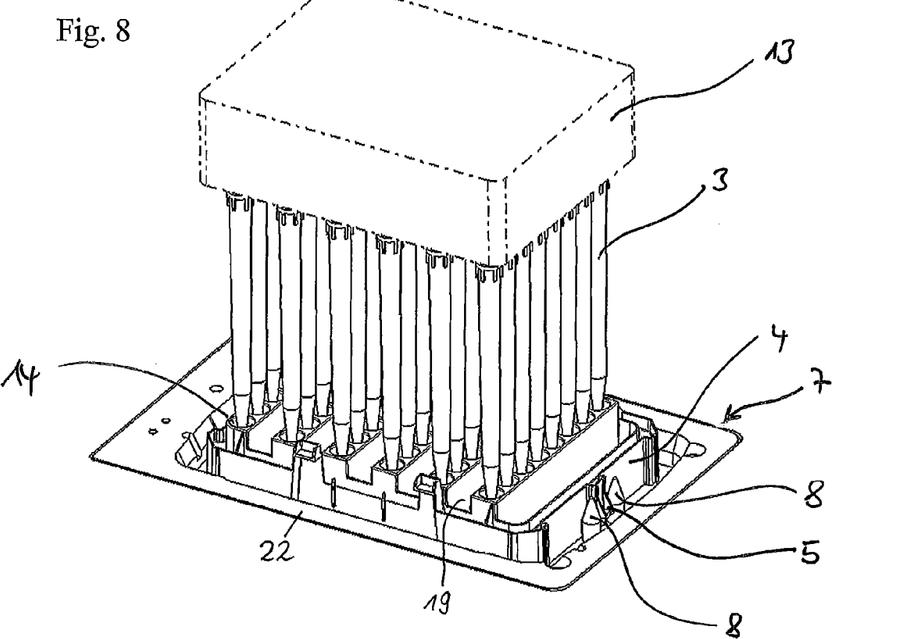
FIG. 8 shows a perspective view of a multichannel pipettor (13) comprising pipet tips (3) above a liquid waste container (7) with a docked contamination prevention shield (4), wherein the pipet tips (3) are introduced into the channels (14) of the contamination prevention shield (4).

FIG. 8: In this depiction, the pipet tips (3) have been introduced into the channels (14) of the contamination prevention shield (4). It can be seen that the cavities (19) between the channels (14) of the contamination prevention shield (4) contribute to further reduce the risk of cross-contamination between the pipet tips (3).

Figure 9:
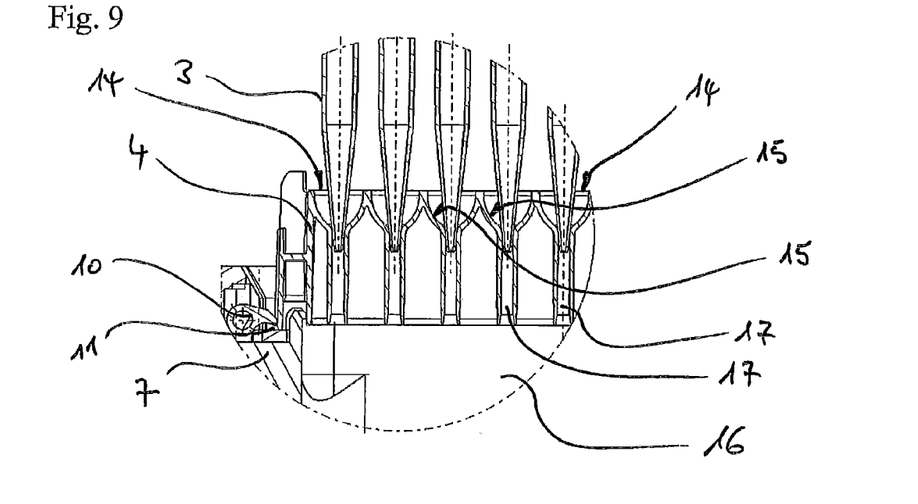
FIG. 9 shows a cross-section view of the contamination prevention shield (4) in the setup of FIG. 8, multichannel pipettor comprising pipet tips (3) above a liquid waste container (7) with a contamination prevention shield (4), wherein the pipet tips (3) are introduced into the channels (14) of the contamination prevention shield (4).

FIG. 9: This closed-up cross-section of the process waste insert (4) in the setup of FIG. 8 shows the pipet tips (3) within the channels (14). The tips (3) have been centered upon introduction by the intake guides (15) and protrude partly into the flow-through channels (17), the diameter of which does not allow a farther introduction of the tips (3).

FIGS. 10-13 depict the release process of the contamination prevention shield (4) from the rack (2) of the tip rack assembly (1) while docking said shield (4) to the liquid waste container (7).

FIGS. 14-17 show a cross-sectional view of the release process of the contamination prevention shield (4) from the rack (2) of the tip rack assembly (1) while docking to the liquid waste container (7). The depicted process is the same as in FIGS. 10-13.

Figure 10:
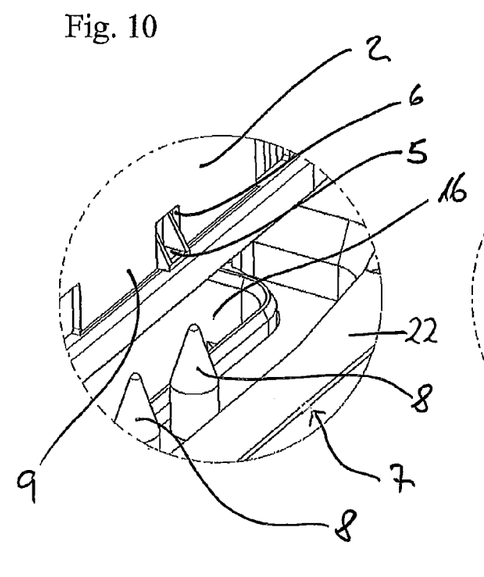
FIGS. 10-13 show cross-section views of the release process of the contamination prevention shield (4) from the rack (2) of the tip rack assembly (1) while docking to the liquid waste container (7).
Figure 14:
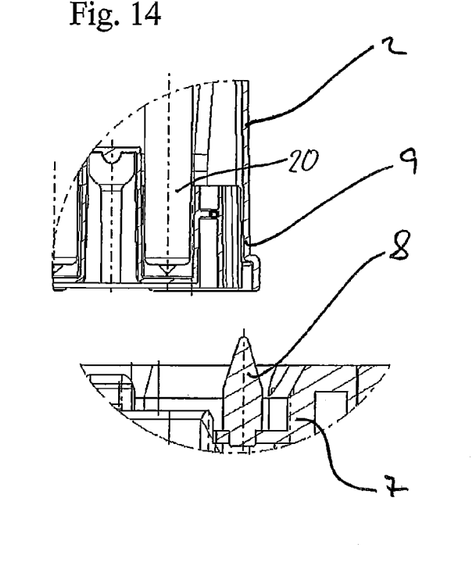
FIGS. 14-17 shows cross-section views of the release process of the contamination prevention shield (4) from the rack (2) of the tip rack assembly (1) while docking to the liquid waste container (7).
Figure 15:
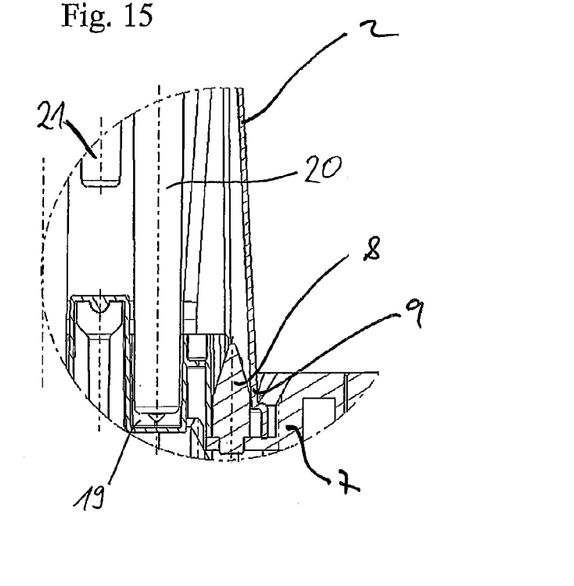

FIG. 10/14: In this zoomed view, the tip rack assembly (1) is about to reversibly dock the contamination prevention shield (4) to the liquid waste container (7). The shield (4) is still removably fixed to the tip rack (2) via the connection between the shield's snap-fit (5) and the rack's recess (6). In this embodiment, said tip rack (2) comprises shorter (21) and longer (20) receptacles for shorter and longer pipet tips, respectively. As can be seen in FIG. 15, the shorter receptacles (21) are situated above the channels (14) so they do not interfere with them in the docked state. As shown in FIG. 14, the cavities (19) mentioned above not only contribute to reducing the risk of cross-contamination, but also serve as recesses for receiving the longer pipet tip receptacles (20) of the tip rack (2). The conical pins (8) of the liquid waste container (7) are about to interact with the shorter side wall (9) of the tip rack (2).

Figure 11:
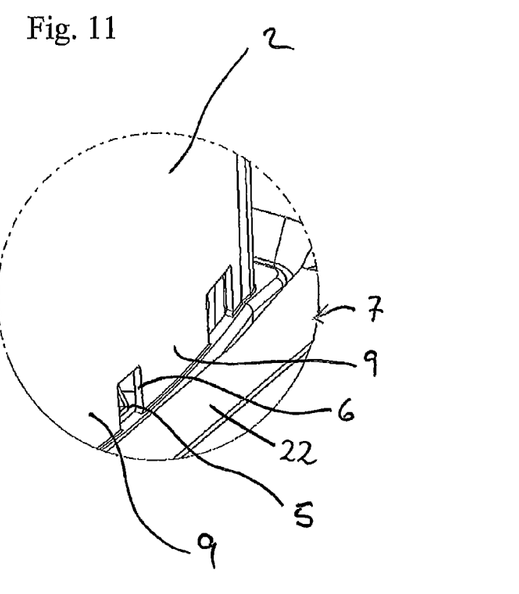

FIG. 11/15: Starting from the setup shown in FIG. 10, the contamination prevention shield (4) is now being reversibly docked to the liquid waste container (7). By extending the shorter side wall (9) of the tip rack (2), the conical pins (8, concealed) facilitate the release of the connection between the shield's snap-fit (5) and the rack's recess (6), thereby removing the contamination prevention shield (4) from the tip rack (2).

Figure 12:
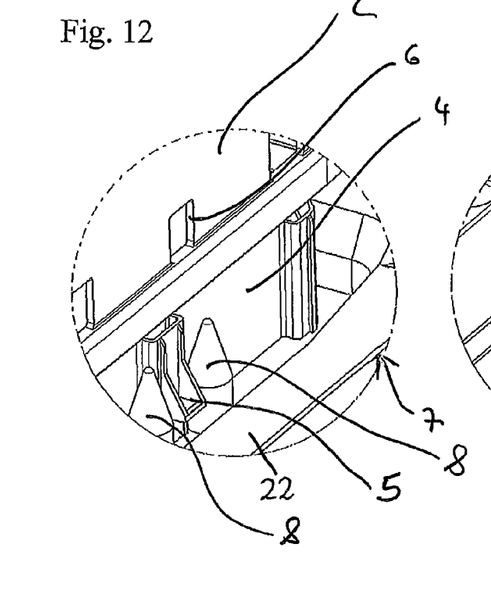
Figure 16:
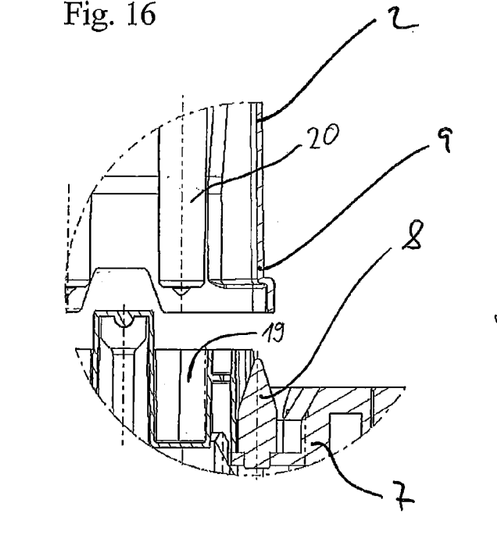

FIG. 12/16: The tip rack (2) is being removed from the liquid waste container (7) in vertical direction, leaving the contamination prevention shield (4) reversibly docked to the liquid waste container (7).

Figure 13:
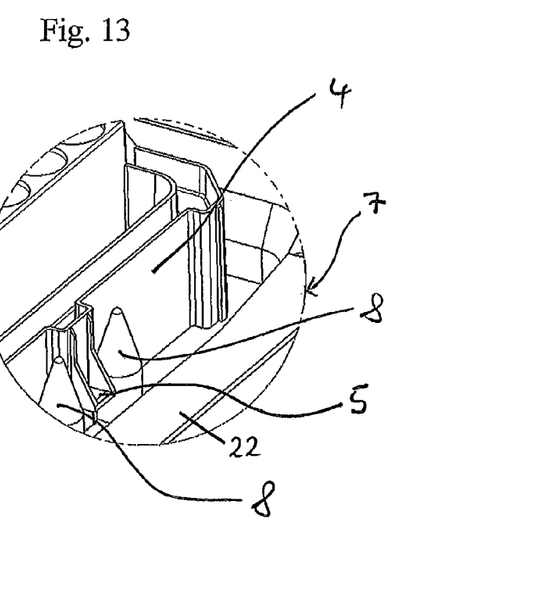
Figure 17:
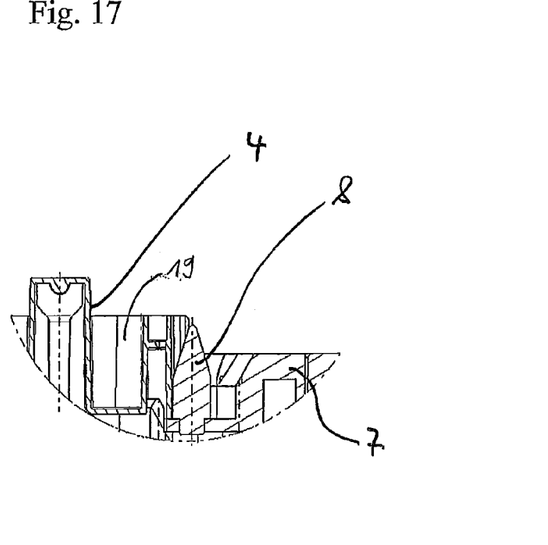

FIG. 13/17: In this depiction, the tip rack (2) is not visible anymore.

FIGS. 18-21 show the reversible docking process of the contamination prevention shield (4) to the liquid waste container (7) in a perspective view.

FIGS. 22-25 show a cross-sectional view of the reversible docking process of the contamination prevention shield (4) to the liquid waste container (7). The depicted process is the same as in FIGS. 18-21.

Figure 18:
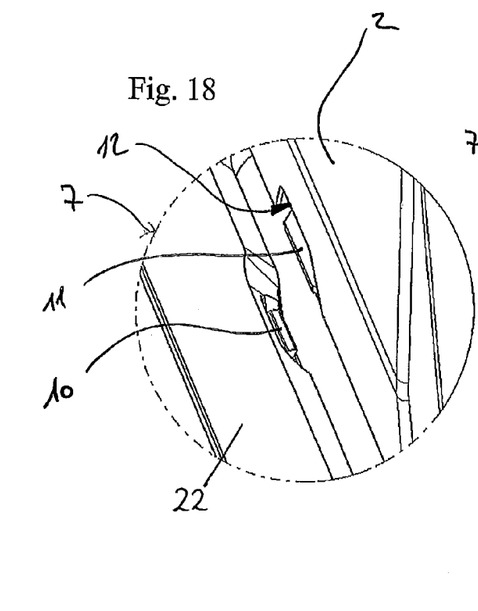
FIGS. 18-21 show cross-section views of the docking process of the contamination prevention shield (4) to the liquid waste container (7).
Figure 22:
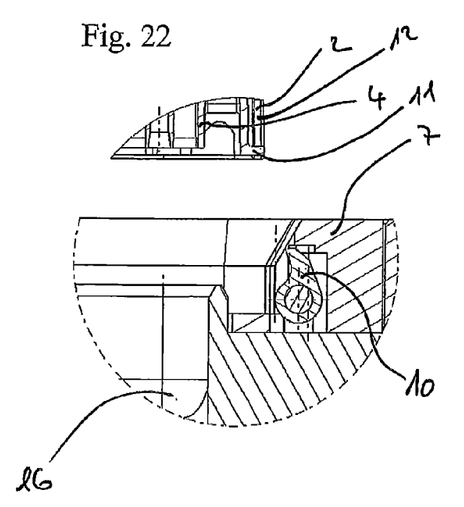
FIGS. 22-25 show cross-section views of the docking process of the contamination prevention shield (4) to the liquid waste container (7).

FIG. 18/22: The contamination prevention shield (4), in this figure still removably fixed to the tip rack (2), is about to be reversibly docked to the liquid waste container (7). This depiction is a zoomed view of the holding-down clamp (10) of the liquid waste container (7) and the corresponding mounting link (11) of the contamination prevention shield (4).

Figure 19:
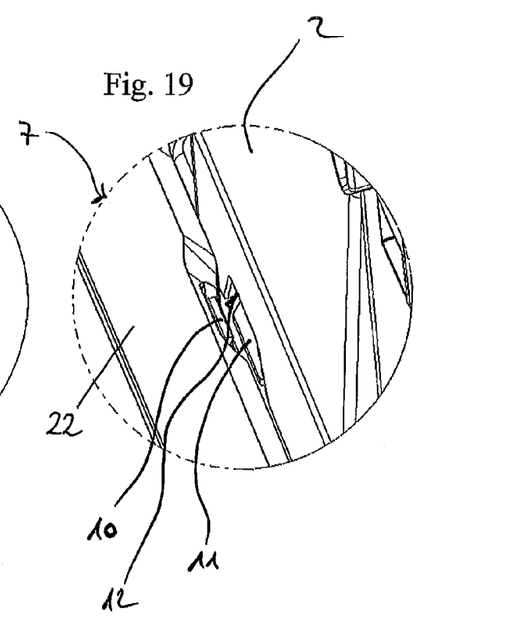
Figure 23:
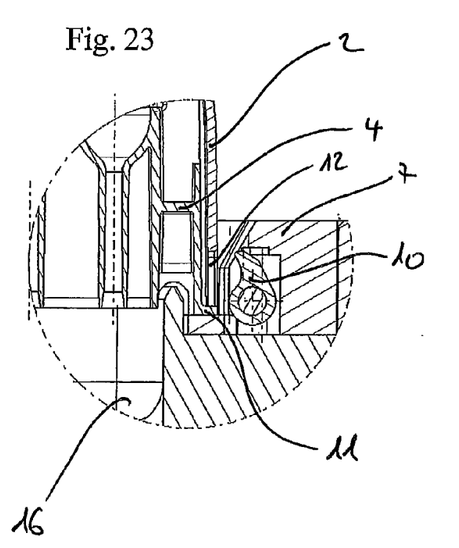

FIG. 19/23: The contamination prevention shield (4) is being docked to the liquid waste container (7), while the cut-outs (12) ensure that the holding-down clamp (10) does not interfere with the tip rack (2), but only with the mounting link (11) of the contamination prevention shield (4). Said cut-outs (12) further prevent the mounting links (11) from colliding with the wall of said tip rack (2).

Figure 20:
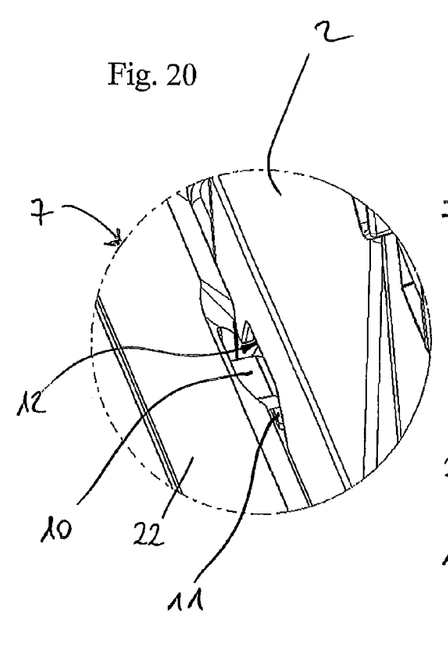
Figure 24:
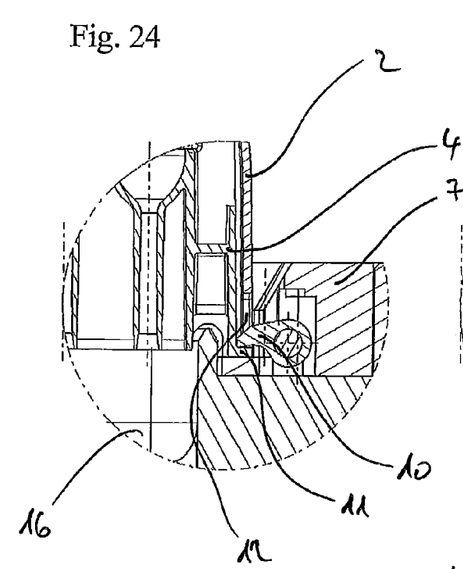

FIG. 20/24: Upon pressing the contamination prevention shield (4) on the rim (22) of the liquid waste container (7), the holding-down clamp (10) of the liquid waste container (7) has been tilted along its pivot mounting and holds down the mounting link (11) of the contamination prevention shield (4), thus reversibly docking the latter to the liquid waste container (7).

Figure 21:
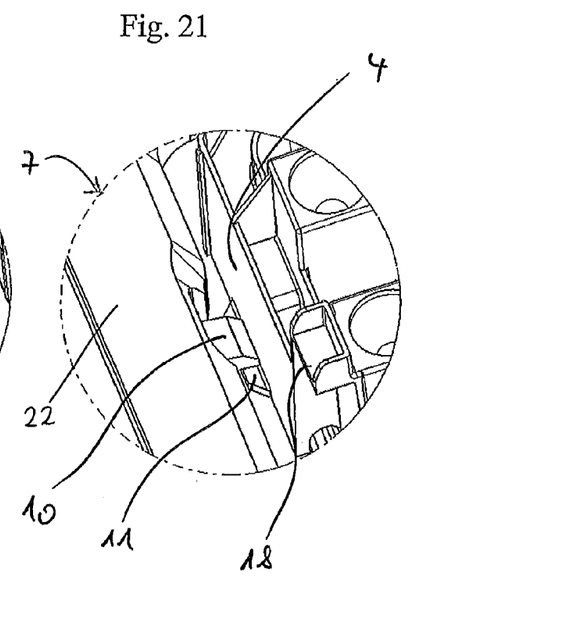
Figure 25:
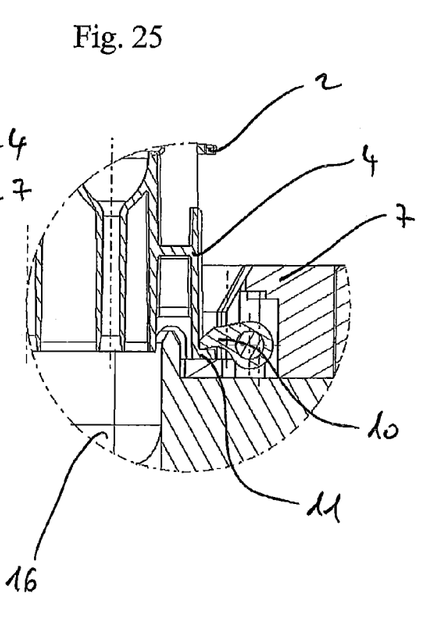

FIG. 21/25: The tip rack (2) has been moved away from the contamination prevention shield (4) reversibly docked to the liquid waste container (7). After one or more uses, the shield (4) can now be removed from the liquid waste container (7) again and discarded separately. A fresh contamination prevention shield may then be reversibly docked to the liquid waste container (7).

Figure 26:
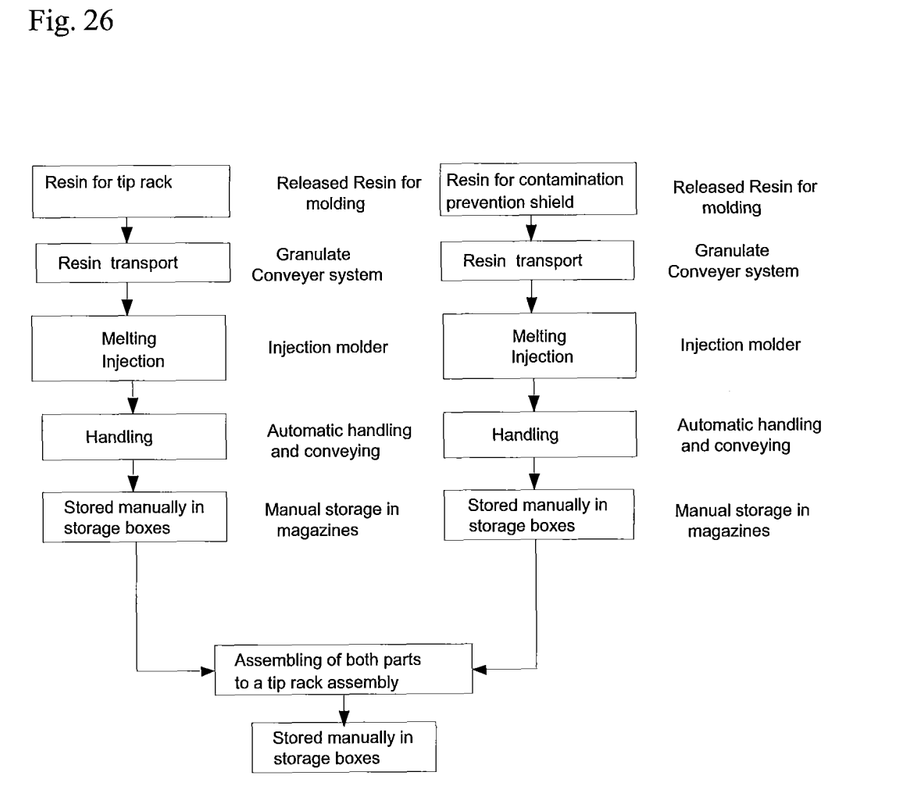
FIG. 26 shows a schematic overview of a production method for the tip rack (2), the contamination prevention shield (4) and the tip rack assembly (1).

FIG. 26 provides a schematic overview of a production method for the tip rack (2), the contamination prevention shield (4) and the tip rack assembly (1). The production of the tip rack (2) is depicted on the left-hand side, the production of the contamination prevention shield (4) on the right-hand side.

What is claimed:

1. An analytical system for processing fluid biological samples, said system comprising: a tip rack assembly, a pipetting device comprising a pipet array, a waste station comprising a liquid waste container, and a transferring device for transporting said tip rack assembly or a component thereof between different units of said system,
   wherein said tip rack assembly comprises an upper part including a rack with multiple receptacles adapted for storing pipet tips, and a bottom part including a contamination prevention shield comprising channels which are geometrically arranged in columns and rows for the introduction of said pipet tips, wherein said channels form contamination barriers between said pipet tips, said columns of channels are separated by cavities for reducing the risk of cross-contamination, and said contamination prevention shield is removably fixed to said rack, and
   wherein said liquid waste container comprises a mechanism to release the contamination prevention shield from the rack of the tip rack assembly and the liquid waste container is adapted for reversibly docking to said contamination prevention shield.

2. The analytical system of claim 1, wherein said mechanism comprises one or more conical pins.

3. The analytical system of claim 1, wherein the liquid waste container comprises a mechanism to reversibly dock the contamination prevention shield to the liquid waste container.

4. The analytical system of claim 3, wherein said mechanism comprises one or more latches or clamps.

5. The analytical system of claim 1, wherein the contamination prevention shield comprises snap-fit elements that are hooked to corresponding recesses on said rack, thereby removably fixing said contamination prevention shield to said rack.

6. The analytical system of claim 1, wherein a part or all of the multiple receptacles of said rack contain disposable pipet tips.

7. The analytical system of claim 1, wherein said channels are geometrically arranged such that a channel is provided for each pipet tip, wherein each pipet tip is attached to a multichannel pipettor.

8. The analytical system of claim 1, wherein each of said channels forms a funnel for centering each of said pipet tips within said channels.

9. The analytical system of claim 1, further comprising one or more elements selected from the group consisting of:
   a reaction module containing the components of a chemical and/or biochemical reaction
   a detection module for detecting signals evoked by an analyte, and
   a storage module for reagents and/or disposables.

* * * * *